(12) United States Patent
Doherty et al.

(10) Patent No.: US 7,306,789 B2
(45) Date of Patent: *Dec. 11, 2007

(54) METHOD OF STIMULATING HAIR GROWTH USING BENZOPYRANS

(75) Inventors: Niall Stephen Doherty, Stonington, CT (US); Dennis Allen Smith, Kent (GB)

(73) Assignee: Warner-Lambert Company, LLC, Ann Arbor, MI (US)

( * ) Notice: Subject to any disclaimer, the term of this patent is extended or adjusted under 35 U.S.C. 154(b) by 716 days.

This patent is subject to a terminal disclaimer.

(21) Appl. No.: 10/699,895

(22) Filed: Nov. 3, 2003

(65) Prior Publication Data

US 2004/0157856 A1    Aug. 12, 2004

Related U.S. Application Data

(60) Provisional application No. 60/425,686, filed on Nov. 12, 2002.

(51) Int. Cl.
*A61K 8/00* (2006.01)
*A61K 31/35* (2006.01)
*A01N 43/16* (2006.01)

(52) U.S. Cl. ............... 424/70.1; 514/453; 514/456
(58) Field of Classification Search ......... 514/247, 514/253, 255, 256, 264, 456
See application file for complete search history.

(56) References Cited

U.S. PATENT DOCUMENTS 5,912,244 A * 6/1999 MacKenzie et al. ........ 514/247
6,071,938 A   6/2000 MacKenzie et al.
2005/0182065 A1 * 8/2005 Doherty et al. ........ 514/252.01

FOREIGN PATENT DOCUMENTS

| EP | 0 351 720 | 1/1990 |
|---|---|---|
| EP | 0 400 430 | 12/1990 |
| EP | 0 450 415 | 10/1991 |
| EP | 0 547 523 | 6/1993 |
| EP | 0 552 679 | 7/1993 |
| WO | WO 95/04730 | 2/1995 |
| WO | WO 00/21957 | 4/2000 |
| WO | WO 2004/043424 | 5/2004 |

OTHER PUBLICATIONS

Webster et al, The synthesis of the glucuronide metabolite of UK-157,147 using immobilized uridine 5'-diphosphoglucuronyl transferase and traditional organic chemistry techniques, Biocatalysis and Biotransformation, 2001, 19 (1), 69-83. ABS.*
Ethell et al, Use of cloned and expressed human UDP-glucuronsyltransferases for the assessment of human drug conjugation and identification of potential drug interactions, Drug Metabolism and Disposition, 2001, 29(1), 48-53. ABS.*
Buhl et al., "Potassium Channel Conductance: A Mechanism Affecting Hair Growth both In Vitro and In Vivo", J. Invest. Dermatol., 98:315-319, 1992.
Buhl et al., "Potassium Channel Conductance as a Control Mechanism in Hair Follicles", J. Invest. Dermatol., 101:148S-152S, 1993.
Co-pending U.S. Appl. No. 11/572,186, filed Jul. 11, 2005 corresponding to WO06/011046A1.
Co-pending U.S. Appl. No. 11/572,032, filed Jul. 4, 2005 corresponding to WO2006008641.

* cited by examiner

*Primary Examiner*—Alton Pryor
(74) *Attorney, Agent, or Firm*—Gregg C. Benson; J. Michael Dixon

(57) ABSTRACT

The present invention is directed to methods of stimulating hair growth by administering particular benzopyran compounds.

13 Claims, 1 Drawing Sheet

METHOD OF STIMULATING HAIR GROWTH USING BENZOPYRANS

CROSS-REFERENCE TO RELATED APPLICATION

This application claims the benefit of U.S. Provisional Application No. 60/425,686 filed Nov. 12, 2002.

BACKGROUND OF THE INVENTION

1. Field of the Invention

The invention is related to the field of treating hair loss. In particular, the invention relates to the use of particular benzopyran compounds to stimulate hair growth and/or prevent hair loss in mammals.

2. Summary of the Related Art

Alopecia, or hair loss, is a common cosmetic problem that can also cause serious negative psychological effects. Hair growth is cyclical, occurring in three stages: anagen, the active growth phase; catagen, the degenerative phase; and telogen, the resting phase. After telogen, the old hair fiber is shed and a new hair is generated as part of the repeating cycle. Alopecia, or hair loss, occurs in both men and women, and is attributed to numerous causes including aging, hormone levels, stress, and chemotherapy. In these circumstances, more and more hair follicles remain in the telogen stage, resulting in a gradual decrease of the hair fiber length and diameter, finally reaching a stage of partial or complete baldness.

Various types of hair loss are known, including alopecia areata, androgenetic alopecia, anagen effluvium, self-induced hair loss, telogen effluvium, and scarring alopecia. Alopecia areata, thought to be an auto-immune disorder, begins with hair loss in a rounded patch on the scalp. Alopecia areata includes mild patchy hair loss on the scalp, as well the loss of all scalp hair, known as alopecia totalis, and the loss of all scalp and body hair, known as alopecia universalis. Androgenetic alopecia, including male and female pattern baldness, is thought to be caused by a combination of genetic predisposition, aging, and androgen hormone levels. Androgenetic alopecia is associated with increased androgen stimulation, which adversely affects the hair follicles. Increased androgen stimulation can be produced by, among other mechanisms, elevated levels of 5-alpha-reductase, an enzyme that converts testosterone to dihydrotestosterone. Anagen effluvium is hair loss due to chemicals or radiation, such as chemotherapy or radiation treatment for cancer. Self-induced hair loss includes hair loss caused by conscious or unconscious self-inflicted damage to the hair. Two common types of self-induced hair loss are trichotillomania, or hair loss that results when someone continually pulls or plucks out his own hair, and traction alopecia, which is caused by hairstyles such as ponytails or braids that continually pull at the hair. Telogen effluvium is stress-related hair loss caused by events such as, for example, surgery, child birth, or pregnancy termination. Further causes of telogen effluvium include the use of oral contraceptives or other prescription drugs, thyroid abnormality, diabetes, lupus, and emotional stress. Scarring alopecia includes hair loss caused by infection and inflammation of the hair follicles, and hair loss caused by burns or other trauma.

Because hair loss is a widespread problem that is considered cosmetically unappealing and often causes emotional distress, there is great demand for alopecia treatments. Many compositions have been tested for their ability to stimulate hair growth, for example, by promoting or prolonging anagen. Examples of such compositions include potassium channel openers, such as minoxidil (Rogaine®, Pharmacia Corp.) and diazoxide; 5-alpha-reductase inhibitors, such as finasteride (Propecia®, Merck & Co.); and the immunosuppressant cyclosporin A. However, known treatments for stimulating hair growth exhibit limited effectiveness and cause unwanted side effects. For example, among other undesirable side effects, potassium channel openers cause cardiovascular effects, finasteride is unsafe for women who are pregnant or may become pregnant, and cyclosporin A suppresses the immune system. Further, even when applied topically to areas in which hair growth is desired, known treatments for alopecia often cause hair growth in undesired areas of the body, such as facial hair on women. Such disadvantages of known compositions for treating alopecia lead many individuals experiencing hair loss to rely on wigs and toupees. Other individuals seek hair transplant surgery, which is expensive, is not fully effective, and sometimes is not possible, for example, for chemotherapy patients. Accordingly, there is a need for new agents for treating alopecia that are safe and effective and stimulate hair growth only in desired areas.

SUMMARY OF THE INVENTION

The present invention addresses the foregoing need by providing methods of treating alopecia by administering particular benzopyran compounds that act as potassium channel openers. Treatment of alopecia according to the methods of the invention is safe for both males and females, and affords reduced cardiovascular effects and reduced stimulation of undesired hair growth outside the area of administration.

Accordingly, in one aspect, the invention provides a method of treating an alopecia selected from the group consisting of alopecia areata, female pattern hair loss, hair loss secondary to chemotherapy or radiation treatment, stress-related hair loss, self-induced hair loss, scarring alopecia, and alopecia in non-human mammals. The method comprises administering to a mammal who has experienced or is considered at risk for experiencing the alopecia an effective amount of a compound of formula (I):

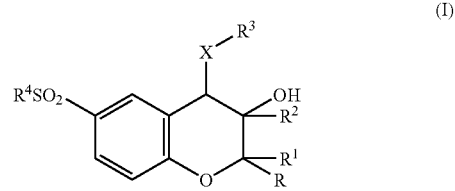

or a pharmaceutically acceptable salt thereof, wherein

X is O, S or NH;

R and $R^1$ are each independently selected from H and $C_1$-$C_4$ alkyl or taken together represent $C_2$-$C_6$ alkylene;

$R^2$ is H or $C_1$-$C_4$ alkyl;

$R^3$ is (a) a 6-membered heterocyclic ring containing 1 or 2 N heteroatoms, said ring being linked to X by a ring carbon atom, optionally benzo-fused and optionally substituted, including in the benzo-fused portion, by $C_1$-$C_6$ alkyl, hydroxy, —$OR^5$, halo, —$S(O)_mR^5$, oxo, amino, —$NHR^5$, —$N(R^5)_2$, cyano, —$CO_2R^5$, —CONH₂, —CONHR⁵, or —CON(R⁵)₂, with the proviso that R³ is not an N—(C₁-C₆ alkyl)pyridonyl group;

(b) when X is NH, a group of the formula:

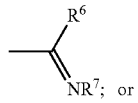

(c) when X is NH, a group of the formula:

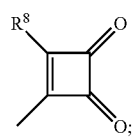

R⁴ is phenyl substituted by a hydroxy group and optionally further substituted by 1 or 2 substituents each independently selected from hydroxy, C₁-C₆ alkyl, —OR⁵, halo, cyano and nitro;

R⁵ is C₁-C₆ alkyl;

R⁶ is —OR⁵, —NHR⁵, —N(R⁵)₂, —SR⁵ or —NHR⁹;

R⁷ is cyano;

R⁸ is —OR⁵, —NHR⁵, —N(R⁵)₂ or —NHR⁹;

R⁹ is phenyl optionally substituted by C₁-C₆ alkyl, hydroxy, —OR⁵, halo, cyano or nitro; and m is 0, 1, or 2.

In some embodiments of the method, R³ is a 6-membered heterocyclic ring containing 2N heteroatoms, said ring being linked to X by a ring carbon atom, optionally benzo-fused and optionally substituted, including in the benzo-fused portion, by C₁-C₆ alkyl, hydroxy, —OR⁵, halo, —S(O)ₘR⁵, oxo, amino, —NHR⁵, —N(R⁵)₂, cyano, —CO₂R⁵, —CONH₂, —CONHR⁵, or —CON(R⁵)₂, with the proviso that R³ is not an N—(C₁-C₆ alkyl)pyridonyl group.

In certain embodiments,

X is O or NH;

R, R¹, and R² are each C₁-C₄ alkyl;

R³ is a 6-membered heterocyclic ring containing 2N heteroatoms, said ring being optionally benzo-fused and optionally substituted, including in the benzo-fused portion, by C₁-C₄ alkyl, hydroxy, halo, or oxo;

R⁴ is phenyl substituted by 1 or 2 hydroxy groups.

In particular embodiments,

X is O;

R, R¹, and R² are each methyl;

R³ is 3-hydroxypridazin-6-yl, 2,3-dihydro-2-methyl-3-oxopyridazin-6-yl, 2,3-dihydro-2ethyl-3-oxopyridazin-6-yl, 1,2-dihydro-1-oxo-2H-phthalazin-4-yl, 1,2-dihydro-2-methyl-1-oxophthalazin-4-yl, or 2-chloropyrimidin-4-yl; and R⁴ is 2-hydroxyphenyl, 3-hydroxyphenyl, 4-hydroxyphenyl or 3,4-dihydroxyphenyl.

In specific embodiments, R³ is 2,3-dihydro-2-methyl-3-oxopyridazin-6-yl and R⁴ is 3-hydroxypheny or 4-hydroxyphenyl.

In some embodiments of the method, the compound of formula (I) has the configuration shown in formula (IA):

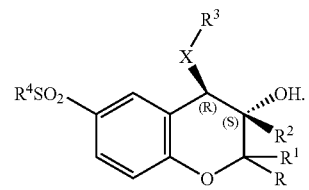

In certain embodiments, the compound of formula (I) is selected from the group consisting of 3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran; 3,4-dihydro-4-(2,3-dihydro-2-methyl-3-oxopyridazin-6-yl)oxy-3-hydroxy-6-(4-hydroxyphenyl)sulphonyl-2,2,3-trimethyl-2H-benzo[b]pyran; and (3S,4R)-stereoisomeric forms thereof.

In particular embodiments, the compound of formula (I) is (3S,4R)-3,4-dihydro-4-(2,3-dihydro-2-methyl-3-oxopyridazin-6-yl)oxy-3-hydroxy-6-(3-hydroxyphenyl)sulphonyl-1-2,2,3-trimethyl-2H-benzo[b]pyran of formula (II):

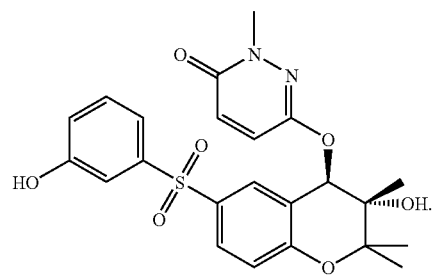

In some embodiments of the method, the compound of formula (I) or a pharmaceutically acceptable salt thereof is administered in the form of a composition further comprising a pharmaceutically acceptable carrier, diluent, or excipient. In certain embodiments, the composition is administered topically to a target area on the mammal. In some embodiments, the composition is removed from the target area after administration.

In certain embodiments of the method, the mammal is a human. In particular embodiments, the alopecia treated is selected from the group consisting of alopecia areata, female pattern hair loss, hair loss secondary to chemotherapy or radiation treatment, stress-related hair loss, self-induced hair loss, and scarring alopecia. In some embodiments, the mammal is non-human.

The term "stimulating hair growth," as used herein, encompasses not only promoting hair growth, but also preventing, arresting, and/or reversing hair loss. "Promoting hair growth" includes stimulating an increase in total hair mass and/or length. Such increase includes increased length and/or growth rate of hair shafts, increased number of hairs, and/or increased hair thickness. Some or all of the above end results can be achieved by prolonging or activating anagen, the growth phase of the hair cycle, or by shortening or delaying the catagen and telogen phases. The term "alopecia," as used herein, encompasses partial or full baldness, hair loss, and/or hair thinning. "Treating alopecia" refers to stimulating hair growth in mammals who have experienced or are considered at risk for experiencing alopecia. The term "mammal" includes humans. As used herein, "pharmaceutically acceptable" means suitable for use in mammals.

DETAILED DESCRIPTION

Figure 1:
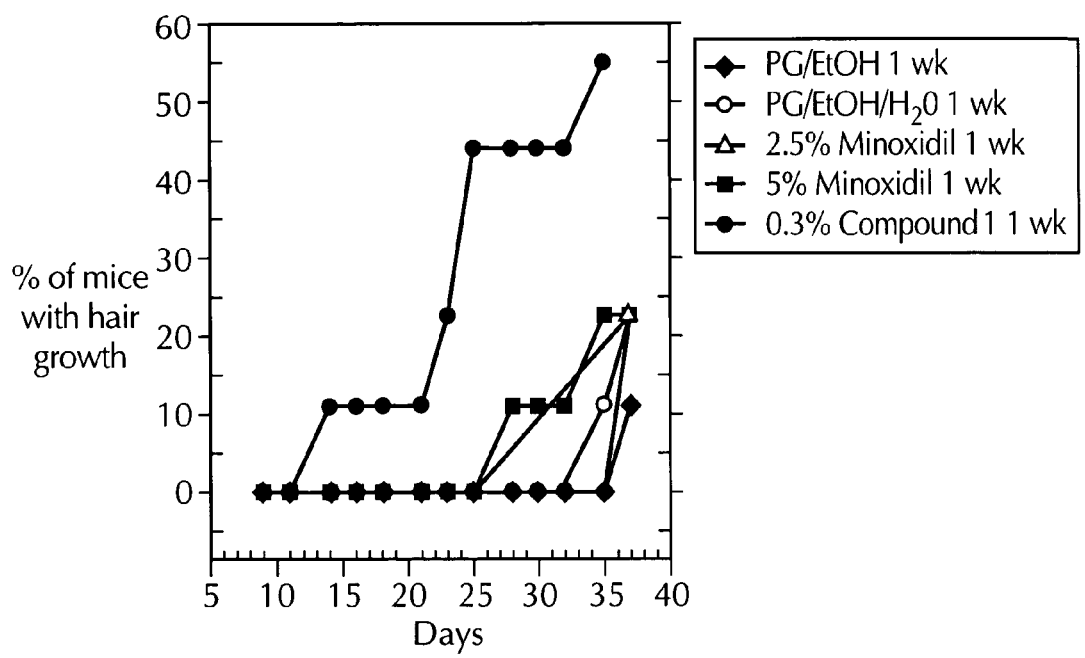
FIG. 1 is a graphic representation illustrating the percentage of female C3H mice (n=9) exhibiting hair growth a given number of days following treatment topically once daily for five days (ending on day 5) with a benzopyran compound as described herein (0.3%), minoxidil (2.5% or 5%), or vehicle control (propylene glycol/ethanol or propylene glycol/ethanol/water).

The issued patents, published patent applications, and literature references cited herein are hereby incorporated by reference to the same extent as if each were specifically and individually indicated to be incorporated by reference. Any inconsistency between these publications and the present disclosure shall be resolved in favor of the present disclosure.

The present invention provides methods of stimulating hair growth by administering particular benzopyran compounds that act as potassium channel openers. The benzopyran compounds used according to the methods of the invention are safe for general use by both males and females. These benzopyran compounds are rapidly metabolized, and therefore cause reduced cardiovascular effects as compared to other known potassium channel openers.

The methods of the invention include stimulating hair growth by administering to a mammal a benzopyran compound of formula (I):

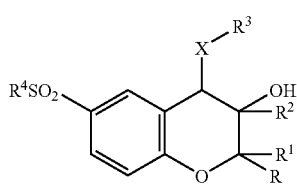

(I)

or a pharmaceutically acceptable salt thereof, wherein X is O, S or NH;

R and $R^1$ are each independently selected from H and $C_1$-$C_4$ alkyl or taken together represent $C_2$-$C_6$ alkylene;

$R^2$ is H or $C_1$-$C_4$ alkyl;

$R^3$ is (a) a 6-membered heterocyclic ring containing 1 or 2 N heteroatoms, said ring being linked to X by a ring carbon atom, optionally benzo-fused and optionally substituted, including in the benzo-fused portion, by $C_1$-$C_6$ alkyl, hydroxy, —$OR^5$, halo, —$S(O)_mR^5$, oxo, amino, —$NHR^5$, —$N(R^5)_2$, cyano, —$CO_2R^5$, —$CONH_2$, —$CONHR^5$, or —$CON(R^5)_2$, with the proviso that $R^3$ is not an N—($C_1$-$C_6$ alkyl)pyridonyl group;

(b) when X is NH, a group of the formula:

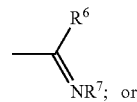

(c) when X is NH, a group of the formula:

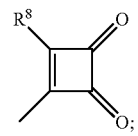

$R^4$ is phenyl substituted by a hydroxy group and optionally further substituted by 1 or 2 substituents each independently selected from hydroxy, $C_1$-$C_6$ alkyl, —$OR^5$, halo, cyano and nitro;

$R^5$ is $C_1$-$C_6$ alkyl;

$R^6$ is —$OR^5$, —$NHR^5$, —$N(R^5)_2$, —$SR^5$ or —$NHR^9$;

$R^7$ is cyano;

$R^8$ is —$OR^5$, —$NHR^5$, —$N(R^5)_2$ or —$NHR^9$;

$R^9$ is phenyl optionally substituted by $C_1$-$C_6$ alkyl, hydroxy, —$OR^5$, halo, cyano or nitro; and m is 0, 1 or 2.

In the above definitions, the term "halo" means fluoro, chloro, bromo, or iodo. Alkyl groups containing three or more carbon atoms may be straight- or branched-chain. In some embodiments, X is O or NH. In particular embodiments, X is O. In some embodiments, R, $R^1$ and $R^2$ are each $C_1$-$C_4$ alkyl. In certain embodiments, R, $R^1$ and $R^2$ are each methyl. In particular embodiments, $R^3$ is a 6-membered heterocyclic ring containing 2N heteroatoms, said ring being linked to X by a ring carbon atom, optionally benzo-fused and optionally substituted, including in the benzo-fused portion, by $C_1$-$C_6$ alkyl, hydroxy, —$OR^5$, halo, —$S(O)_mR^5$, oxo, amino, —$NHR^5$, —$N(R^5)_2$, cyano, —$CO_2R^5$, —$CONH_2$, —$CONHR^5$, or —$CON(R^5)_2$, with the proviso that $R^3$ is not an N—($C_1$-$C_6$ alkyl)pyridonyl group. In some embodiments, $R^3$ is (a) a 6-membered heterocyclic ring containing 1 or 2 N heteroatoms, said ring being optionally benzo-fused, optionally substituted by $C_1$-$C_4$ alkyl, hydroxy, halo, or oxo, and optionally not fully saturated; or (b) a group of the formula:

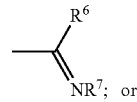

(c) a group of the formula:

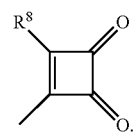

In certain embodiments, $R^3$ is 1,2-dihydro-2-oxo-1H-pyridin-4-yl, 1,2-dihydro-5,6-dimethyl-2-oxo-1H-pyridin-4-yl, 3-hydroxypyridazin-6-yl, 2,3-dihydro-2-methyl-3-oxopyridazin-6-yl, 2,3-dihydro-2-ethyl-3-oxopyridazin-6-yl, 1,2-dihydro-1-oxo-2H-phthalazin-4-yl, 1,2-dihydro-2-methyl-1-oxophthalazin-4-yl, 2-chloropyrimidin-4-yl, 3,4-dioxo-2-ethoxycyclobut-1-en-1-yl or 3-cyano-2-methyl-isothioureido. In specific embodiments, $R^3$ is 1,2-dihydro-2-oxo-1H-pyridin-4-yl or 2,3-dihydro-2-methyl-3-oxopyridazin-6-yl. In some embodiments, $R^4$ is phenyl substituted by one or two hydroxy group(s). In particular embodiments, $R^4$ is 2-, 3- or 4-hydroxyphenyl, or is 3,4-dihydroxyphenyl. In specific embodiments, $R^4$ is 3-hydroxyphenyl or 4-hydroxyphenyl. In some embodiments, $R^6$ is —$SR^5$. In particular embodiments, $R^6$ is methylthio. In some embodiments, $R^8$ is —$OR^5$. In particular embodiments, $R^8$ is ethoxy.

At least some compounds of formula (I) contain one or more asymmetric carbon atoms and thus possess two or more stereoisomeric forms. The methods of the invention encompass the use of the individual stereoisomers, as well as mixtures thereof, together, where appropriate, with all tautomeric forms of the compounds of formula (I). Separation of diastereoisomers is achieved by conventional techniques, such as, for example, fractional crystallization, chromatography, or HPLC of a stereoisomeric mixture of a compound of formula (I) or a suitable salt or derivative thereof. An individual enantiomer of a compound of formula (I) is prepared from a corresponding optically pure intermediate, or by resolution, such as by HPLC of the corresponding racemate using a suitable chiral support or by fractional crystallization of the diastereoisomeric salts formed by reaction of the corresponding racemate with a suitable optically active acid or base.

In some embodiments, the compounds of formula (I) have the configuration shown in formula (IA):

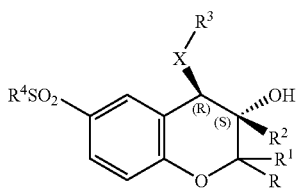

where X, R, $R^1$, $R^2$, $R^3$ and $R^4$ are as previously defined for formula (I). In certain embodiments, the compound of formula (I) is selected from the group consisting of 3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran; 3,4-dihydro-4-(2,3-dihydro-2-methyl-3-oxopyridazin-6-yl)oxy-3-hydroxy-6-(4-hydroxyphenyl)sulphonyl-2,2,3-trimethyl-2H-benzo[b]pyran; and (3S,4R)-stereoisomeric forms thereof. In specific embodiments, the compound of formula (I) is (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran of formula (II):

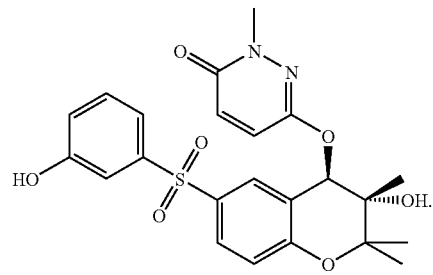

Pharmaceutically acceptable salts of the compounds of formula (I) include acid addition and base salts thereof. Suitable acid addition salts are formed from acids that form non-toxic salts. Non-limiting examples include hydrochloride, hydrobromide, hydroiodide, sulfate, bisulfate, phosphate, hydrogen phosphate, acetate, maleate, fumarate, lactate, tartrate, citrate, gluconate, benzoate, methanesulphonate, benzenesulphonate, and p-toluenesulphonate salts. Suitable base salts are formed from bases which form non-toxic salts. Non-limiting examples include aluminium, calcium, magnesium, zinc and diethanolamine salts. For a review of suitable salts, see Berge et al., *J. Pharm. Sci.* 66:1-19 (1977).

Compounds of formula (I) and pharmaceutically acceptable salts thereof are prepared according to techniques known in the art. For example, the compounds are prepared as described in U.S. Pat. Nos. 5,912,244 and 6,071,938.

The methods of the invention are useful for stimulating hair growth, i.e., preventing, arresting, and/or reversing hair loss, as well as promoting hair growth, in male and female mammals. In some embodiments the mammal is a human. The methods of the invention also are useful for treating other mammals such as, for example, dogs, cats, and sheep. Treatment of such mammals includes, but is not limited to, preventing, arresting, or reversing hair loss due to mange or other causes, as well as enhancing wool or pelt production. The invention includes methods of treating alopecia in mammals who have experienced or are considered at risk for experiencing partial or full baldness, hair loss, or hair thinning. Types of alopecia suitable for treatment according to the methods of the invention include, but are not limited to, alopecia areata, including alopecia totalis and alopecia universalis; androgenetic alopecia; anagen effluvium, or hair loss due to chemicals or radiation, such as chemotherapy or radiation treatment for cancer; self-induced hair loss, such as trichotillomania or traction alopecia; telogen effluvium, or stress-related hair loss caused by events such as, for example, surgery, child birth, pregnancy termination, use of oral contraceptives or other prescription drugs, thyroid abnormality, diabetes, lupus, or emotional stress; scarring alopecia, such as hair loss caused by infection and inflammation of the hair follicles, or hair loss caused by burns or other trauma; and alopecia in non-human mammals. In some embodiments, methods of the invention are used to treat alopecia areata, female pattern hair loss, hair loss secondary to chemotherapy or radiation treatment, stress-related hair loss, self-induced hair loss, scarring alopecia, or alopecia in non-human mammals. In particular embodiments, methods of the invention are used to treat alopecia areata. In certain embodiments, methods of the invention are used to treat female pattern hair loss.

According to the methods of the invention, hair growth is stimulated by administering to a subject an effective amount of a compound of formula (I), or a pharmaceutically acceptable salt thereof. An effective amount is an amount sufficient to stimulate hair growth in a mammal treated with the compound. One of skill in the art will understand that effective amounts vary based on factors including the species, sex, age, body surface area, weight, and physical condition of the mammal being treated, as well as the chosen route of administration, the use of pharmaceutical carriers, diluents, or excipients, and any cotherapy, for example, coadministration of additional agents for promoting hair growth. A physician or veterinarian uses standard techniques known in the art to determine the dosage and frequency of administration of a benzopyran compound to stimulate hair growth according to the methods of the invention. Treatment according to the methods of the invention is continued until the desired hair growth has occurred, and then as needed to sustain such hair growth. When the cause of hair loss is ongoing, such as hair loss due to genetics or aging, treatment is continued indefinitely to maintain hair growth.

In some embodiments, the benzopyran compound is administered topically to a mammal in one or more areas where hair growth is desired, i.e., target areas. When administered topically, the benzopyran compound stimulates hair growth locally in the target area of administration, while causing little undesired hair growth in other areas of the body such as, for example, facial hair in women. Topical administration of the benzopyran compound also allows for reduced cardiovascular effects, as the effect of the benzopyran compound is localized to the area of administration. For example, the compound is administered to the scalp, chest, or face of a human. Alternatively, the compound is administered to bald patches in the coat of an animal, such as a dog or cat, or to the entire coat to improve overall pelt quality in an animal, such as a mink, that is raised for its fur. In some embodiments, the topical formulation is removed from the target area after administration, for example, by rinsing with water or other liquids that are physiologically compatible with the skin. Before removal, the topical formulation is left on the skin for a period of time sufficient for the benzopyran compound to be pharmaceutically effective. For example, the formulation is left on the skin for from about 2 minutes up to about 12 hours before removal.

Any potential side effects of the benzopyran compound are likely reduced due to rapid clearance of the absorbed compound. In vitro metabolism experiments with (3S,4R)-3,4-dehydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran indicate that the rate of conjugation is high, suggesting high plasma clearance in vivo. In vivo experiments in rat, dog, and human demonstrate rapid clearance, corresponding to low exposure to unchanged drug following oral or systemic administration. The compound is cleared by conjugation to produce the glucuronide and sulfate metabolites. The compound and its metabolites are rapidly taken up by the liver and excreted in the bile. Thus, following topical administration, any absorbed benzopyran is subject to high hepatic extraction, and thus low systemic exposure.

Compositions including a compound of formula (I), or a pharmaceutically acceptable salt thereof, are formulated for topical administration according to standard techniques known in the art (see, e.g., *Remington's Pharmaceutical Sciences*, 17th ed., Mack Publishing Co. (1990); *Pharmaceutical Dosage Forms and Drug Delivery Systems*, 6th ed., Williams & Wilkins (1995)). Non-limiting examples of conventional pharmaceutical formulations for topical administration include gels, ointments, lotions, pastes, jellies, solutions, foams, sprays, aerosols, dusting powders, shampoos, and the like adapted for application to the skin. Topical formulations for use in the methods of the invention include a compound of formula (I), or a pharmaceutically acceptable salt thereof, and a pharmaceutically acceptable carrier, diluent, and/or excipient. Suitable carrier, diluent, and excipient materials are well known in the art (see, e.g., *Remington's Pharmaceutical Sciences*, 17th ed., Mack Publishing Co. (1990)) and include, but are not limited to, water; saline; alcohols; pharmaceutically acceptable gels, such as aloe vera gel; allantoin; glycerine; oils, such as vitamin A and E oils, vegetable oils, and mineral oils; and pharmaceutically acceptable glycols, such as polyethylene glycols and propylene glycol. Sometimes, the composition for topical administration includes other additives known in the art, such as, for example, fragrances and other cosmetic ingredients, penetration enhancement agents, surface active agents, and additional hair growth stimulants. Non-limiting examples of suitable surface active agents, or emulsifying agents, include non-ionic surface active agents, such as, for example, nonylphenoxypolyethoxy ethanol, polyoxyethylene ethers, and block copolymers of ethylene oxide and propylene oxide, and ionic surface active agents, such as, for example, sodium lauryl sulfate and similar compounds (see, e.g., *McCutcheon's Detergents and Emulsifiers*, North American Ed., Allured Publishing Co. (1986)). Suitable penetration enhancement agents include, but are not limited to, 2-methyl propan-2-ol, propan-2-ol, ethyl-2-hydroxypropanoate, hexan-2,5-diol, POE(2)ethyl ether, di(2-hydroxypropyl)ether, pentan-2,4-diol, acetone, POE(2)methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, and 1-dodecylazacyloheptan-2-one. Such agents are commercially available, e.g., from Sigma-Aldrich Corp., St. Louis, Mo.

Additional hair growth stimulants include, but are not limited to, benzalkonium chloride, benzethonium chloride, phenol, estradiol, diphenhydramine hydrochloride, chlorpheniramine maleate, chlorophyllin derivatives, cholesterol, salicylic acid, cysteine, methionine, red pepper tincture, benzyl nicotinate, D,L-menthol, peppermint oil, calcium pantothenate, panthenol, castor oil, hinokitiol, prednisolone, resorcinol, monosaccharides and esterified monosaccharides, chemical activators of protein kinase C enzymes, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, cyclosporins, such as cyclosporin A, potassium channel blockers, such as minoxidil, 5-α-reductase inhibitors, such as finasteride, and androgen receptor antagonists, such as cyproterone acetate. Particularly useful additional hair growth stimulants include minoxidil, finasteride, and cyclosporin A. Additional hair growth stimulants are available from commercial sources including Sigma-Aldrich Corp., St. Louis, Mo.

Further useful additives are set forth, for example, in the *CTFA Cosmetic Ingredient Handbook*, 2nd Ed. (1992), which describes common cosmetic and pharmaceutical ingredients. Non-limiting examples of such ingredients include abrasives, absorbents, aesthetic components such as fragrances and colorants, essential oils, astringents, anti-caking agents, anti-foaming agents, anti-microbial agents, anti-oxidants, binders, biological additives, buffering agents, bulking agents, chelating agents, chemical additives, opacifying agents, pH adjusters, propellants, reducing agents, sequestrants, skin-conditioning agents such as humectants, thickeners, and vitamins.

In some embodiments, compositions for topical administration include a compound of formula (I), or a pharmaceutically acceptable salt thereof, encapsulated in liposomes to aid in delivery to the hair follicle. In certain embodiments, the topical formulation is an ointment such as, for example, a cream, having an oleaginous, absorption, water-soluble, and/or emulsion-type base, e.g., petrolatum, lanolin, polyethylene glycols, and mixtures thereof. In other embodiments, the topical formulation is an emulsion containing a compound of formula (I), or a pharmaceutically acceptable salt thereof, a natural or synthetic lipid or oil, optionally a humectant, such as glycerin, and optionally an ionic or non-ionic emulsifying agent. In still other embodiments, the topical formulation is a gel including a compound of formula (I), or a pharmaceutically acceptable salt thereof, a carbomer, a synthetic, high-molecular weight, cross-linked polymer of acrylic acid, an alcohol, such as ethanol or isopropanol, optionally a pharmaceutically acceptable glycol, such as propylene glycol, and optionally water. Other useful topical formulations include foams or sprays that are applied directly from a suitable container to the area where hair growth is desired without contacting the skin of the hands, thus avoiding the risk of causing undesired hair growth on the hands. Particularly useful topical formulations are absorbed into the skin without leaving a greasy or oily residue on the surrounding area. A non-limiting example of such a formulation is a foam containing a compound of formula (I), or a pharmaceutically acceptable salt thereof; water; one or more alcohols, such as ethanol, cetyl alcohol, and stearyl alcohol; a pharmaceutically acceptable glycol, such as propylene glycol; pharmaceutical additives such as, for example, polysorbate 60, citric acid, and potassium citrate; and a hydrocarbon propellant. The foam is dispensed from a pressurized aluminum can and is broken down rapidly by body heat, leaving little residue on the skin. A formulation for topical administration according to the methods of the invention contains between about 0.005% and about 20.0% by weight, sometimes between 0.005% and about 5.0% by weight, of a compound of formula (I), or a pharmaceutically acceptable salt thereof. In particular embodiments, the formulation contains between about 0.01% and about 5.0% by weight of a compound of formula (I), or a pharmaceutically acceptable salt thereof. The remainder of the formulation is made up of pharmaceutically acceptable carriers, diluents, excipients, and other additives, as set forth above. The dosage and treatment schedule for topical administration is determined by a physician or veterinarian, as described above. For example, in some non-limiting embodiments, between about 100 μg/cm$^2$ and about 3000 μg/cm$^2$ of a topical formulation of benzopyran is applied to the scalp, or other desired body area, of an adult human each day in a single dose or several doses.

The following non-limiting example further illustrates certain embodiments of the invention:

EXAMPLE 1

Mouse Hair Growth Model

The effect of the benzopyran compound (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran (Compound 1) on hair growth was evaluated by topical administration of the compound to mice. Compound 1 may be made according to the methods described in U.S. Pat. Nos. 5,912,244 and 6,071,938.

Female C3H/HeN mice, 42-46 days old (Charles River Laboratories, Raleigh, N.C.) were used for the study. The hair follicles of mice at this age are in the second telogen phase, which usually lasts from 6 to 9 weeks, providing a wide enough window to test compounds for their ability to induce earlier onset of anagen. Only mice with pink skin, a visual indication of the telogen phase, were selected for inclusion in the study.

Test compounds, including Compound 1, the potassium channel opener minoxidil (marketed as Rogaine® containing 2% minoxidil), and cyclosporin A, were dissolved in a vehicle consisting of propylene glycol (30%) and ethanol (70%). A test compound dissolved in vehicle, or a vehicle control (30/70 propylene glycol/ethanol, unless otherwise specified) was applied topically to the clipped dorsal region of the mice in each test group (7-10 mice) in a volume of 20 μl/cm$^2$. Treatments were applied once or twice daily, 5 days/week.

Figure 2:
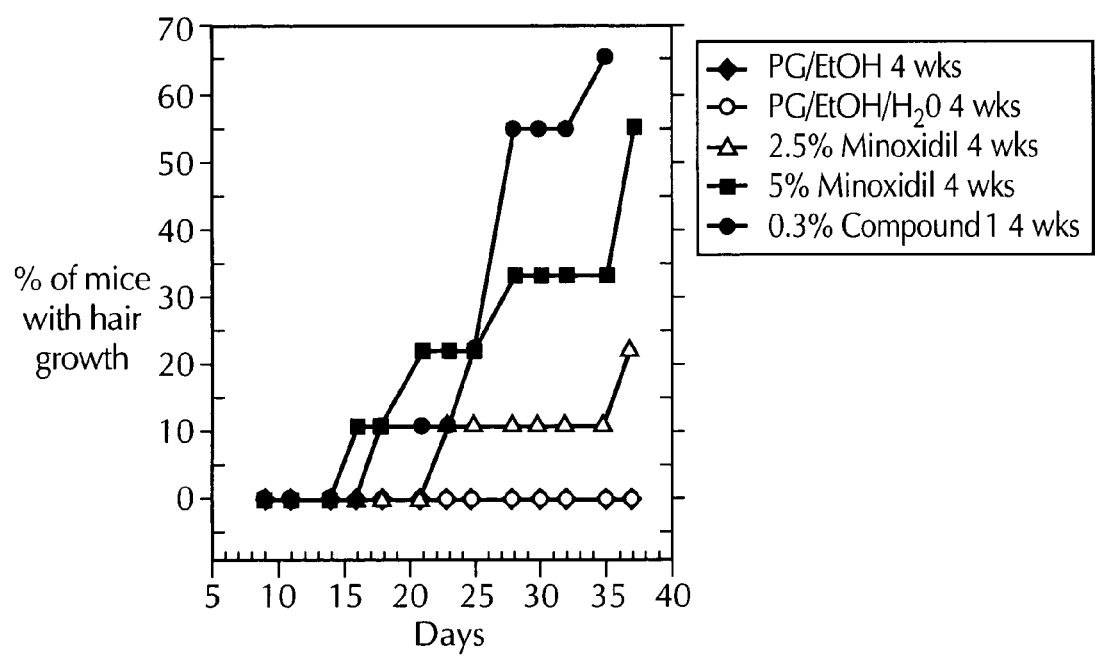
FIG. 2 is a graphic representation illustrating the percentage of female C3H mice (n=9) exhibiting hair growth as a function of time, upon treatment topically once daily five days a week for four weeks (ending on day 28) with a benzopyran compound as described herein (0.3%), minoxidil (2.5% or 5%), or vehicle control (propylene glycol/ethanol or propylene glycol/ethanol/water).

The treatment area was observed and graded for signs of hair growth and local skin irritation. The hair growth response was quantified by recording, for each animal, the day on which signs of hair growth first appeared over the treated area. The first sign of anagen was the darkening of skin color as melanocytes in the follicles started to synthesize melanin in preparation for the production of pigmented hairs. The response time was measured as the number of days following initiation of treatment when hair growth was present in 50% of the mice in a given group. The mice were observed for 35 days or longer. Data are presented in Table I and FIGS. 1 and 2.

TABLE 1

| Treatment Study # | Dose (%) | Doses/ day | Duration (weeks) | \multicolumn{13}{c}{Day on which 50% incidence of hair growth occurred} |
|---|---|---|---|---|---|---|---|---|---|---|---|---|---|---|---|---|
| | | | | 1 | 2 | 3 | 4 | 5 | 6 | 7 | 8 | 9 | 10 | 11 | 12 | 13 |
| Vehicle | — | — | — | >35 | >35 | 21 | 25 | >35 | >35 | >35 | >35 | >35 | >35 | 56 | >35 | 56 |
| Compound 1 | 0.03 | 1 | 1 | | | | | >35 | >35 | >35 | | >35 | | | | |
| Compound 1 | 0.1 | 1 | 1 | | | | | >35 | >35 | | | | | | | |
| Compound 1 | 0.3 | 1 | 1 | | | | 11 | >35 | >35 | 14 | | 16 | 21 | 25 | >35 | 28 |

TABLE 1-continued

| Treatment Study # | Dose (%) | Doses/ day | Duration (weeks) | \multicolumn{13}{c}{Day on which 50% incidence of hair growth occurred} | | | | | | | | | | | | | |
|---|---|---|---|---|---|---|---|---|---|---|---|---|---|---|---|---|
| | | | | 1 | 2 | 3 | 4 | 5 | 6 | 7 | 8 | 9 | 10 | 11 | 12 | 13 |
| Compound 1 | 1 | 1 | 1 | | | 14 | 11 | >35 | | | 21 | 28 | >35 | | 16 | |
| Compound 1 | 1 | 2 | 2 | 25 | 28 | | | | | | | | | | | |
| Compound 1 | 0.3 | 1 | 4 | | | | | | | | | | 23 | | 16 | 35 |
| Compound 1 | 1 | 1 | 4 | | | | | | | | | | >35 | | 18 | |
| Vehicle | | 1 | 1 | | | | | | | | | | | | | 56 |
| Minoxidil | 2.5 | 1 | 1 | | | | | | | | | | | | | 53 |
| Minoxidil | 5 | 1 | 1 | | | | | | | | | | | | | 56 |
| Vehicle | | 1 | 4 | | | | | | | | | | | | | 58 |
| Minoxidil | 2.5 | 1 | 4 | | | | | | | | | | | | | 39 |
| Minoxidil | 5 | 1 | 4 | | | | | | | | | | | | | 37 |
| Cyclosporin A | 0.5 | 1 | 1 | | | | | <9 | | 9 | 9 | 10 | 11 | 11 | 9 | 11 | 39 |

The results indicate that Compound 1 stimulated hair growth when applied topically at 0.3% or 1% once or twice daily for five days or up to 4 weeks. All cases of hair growth stimulation resulted in full and thick hair growth over the treated area. Hair growth was not observed for concentrations lower than 0.3% Compound 1 (0.1% to 0.03%). Concentrations greater than 1% resulted in precipitation of drug on the skin and appeared less efficacious than lower doses. No local irritation or other adverse effects were observed in mice treated for 2 weeks with 5% Compound 1.

EQUIVALENTS

While the foregoing invention has been described in some detail for purposes of clarity and understanding, it will be appreciated by one skilled in the art from a reading of this disclosure that various changes in form and detail can be made without departing from the scope of the invention.

What is claimed is:

1. A method of treating an alopecia selected from the group consisting of alopecia areata, hair loss secondary to chemotherapy or radiation treatment, stress-related hair loss, self-induced hair loss, and scarring alopecia, the method comprising administering to a mammal who has experienced or is considered at risk for experiencing the alopecia an effective amount of a compound of formula (I)

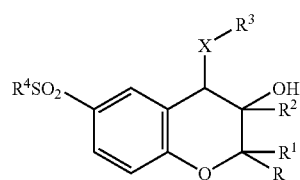

(I)

or a pharmaceutically acceptable salt thereof, wherein

X is O, S or NH;

R and $R^1$ are each independently selected from H and $C_1$-$C_4$ alkyl or taken together represent $C_2$-$C_6$ alkylene;

$R^2$ is H or $C_1$-$C_4$ alkyl;

$R^3$ is (a) a 6-membered heterocyclic ring containing 1 or 2 N heteroatoms, said ring being linked to X by a ring carbon atom, optionally benzo-fused and optionally substituted, including in the benzo-fused portion, by $C_1$-$C_6$ alkyl, hydroxy, —$OR^5$, halo, —$S(O)_mR^5$, oxo, amino, —$NHR^5$, —$N(R^5)_2$, cyano, —$CO_2R^5$, —$CONH_2$, —$CONHR^5$, or —$CON(R^5)_2$, with the proviso that $R^3$ is not an N—($C_1$-$C_6$ alkyl)pyridonyl group;

(b) when X is NH, a group of the formula:

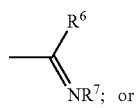

or (c) when X is NH, a group of the formula:

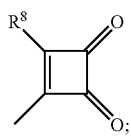

$R^4$ is phenyl substituted by a hydroxy group and optionally further substituted by 1 or 2 substituents each independently selected from hydroxy, $C_1$-$C_6$ alkyl, —$OR^5$, halo, cyano and nitro;

$R^5$ is $C_1$-$C_6$ alkyl;

$R^6$ is —$OR^5$, —$NHR^5$, —$N(R^5)_2$, —$SR^5$ or —$NHR^9$;

$R^7$ is cyano;

$R^8$ is —$OR^5$, —$NHR^5$, —$N(R^5)_2$ or —$NHR^9$;

$R^9$ is phenyl optionally substituted by $C_1$-$C_6$ alkyl, hydroxy, —$OR^5$, halo, cyano or nitro; and m is 0, 1, or 2.

2. The method of claim 1, wherein $R^3$ is a 6-membered heterocyclic ring containing 2N heteroatoms, said ring being linked to X by a ring carbon atom, optionally benzo-fused and optionally substituted, including in the benzo-fused portion, by $C_1$-$C_6$ alkyl, hydroxy, —$OR^5$, halo, —$S(O)_mR^5$, oxo, amino, —$NHR^5$, —$N(R^5)_2$, cyano, —$CO_2R^5$, —$CONH_2$, —$CONHR^5$, or —$CON(R^5)_2$, with the proviso that $R^3$ is not an N—($C_1$-$C_6$ alkyl)pyridonyl group.

3. The method of claim 2, wherein

X is O or NH;

R, $R^1$, and $R^2$ are each $C_1$-$C_4$ alkyl;

$R^3$ is a 6-membered heterocyclic ring containing 2N heteroatoms, said ring being optionally benzo-fused and optionally substituted, including in the benzo-fused portion, by $C_1$-$C_4$ alkyl, hydroxy, halo, or oxo; and $R^4$ is phenyl substituted by 1 or 2 hydroxy groups.

4. The method of claim 3, wherein
X is O;
R, R¹, and R² are each methyl;
R³ is 3-hydroxypridazin-6-yl, 2,3-dihydro-2-methyl-3-oxopyridazin-6-yl, 2,3-dihydro-2 ethyl-3-oxopyridazin-6-yl, 1,2-dihydro-1-oxo-2H-phthalazin-4-yl, 1,2-dihydro-2-methyl-1-oxophthalazin-4-yl, or 2-chloropyrimidin-4-yl; and
R⁴ is 2-hydroxyphenyl, 3-hydroxyphenyl, 4-hydroxyphenyl or 3,4-dihydroxyphenyl.

5. The method of claim 4, wherein R³ is 2,3-dihydro-2-methyl-3-oxopyridazin-6-yl and R⁴ is 3-hydroxyphenyl or 4-hydroxyphenyl.

6. The method of claim 1, wherein the compound of formula (I) has the configuration shown in formula (IA)

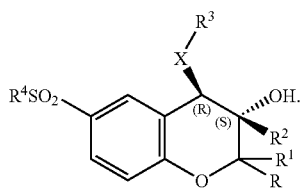

(IA)

7. The method of claim 1, wherein the compound of formula (I) is selected from the group consisting of 3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran; 3,4-dihydro-4-(2,3-dihydro-2-methyl-3-oxopyridazin-6-yl)oxy-3-hydroxy-6-(4-hydroxyphenyl) sulphonyl-2,2,3-trimethyl-2H-benzo[b]pyran; and (3S,4R)-stereoisomeric forms thereof.

8. The method of claim 1, wherein the compound of formula (I) is (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran of formula (II)

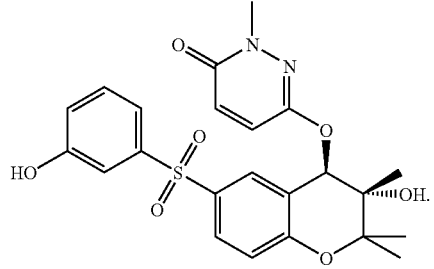

(II)

9. The method of claim 1, wherein the compound of formula (I) or a pharmaceutically acceptable salt thereof is administered in the form of a composition further comprising a pharmaceutically acceptable carrier, diluent, or excipient.

10. The method of claim 9, wherein the composition is administered topically to a target area on the mammal.

11. The method of claim 10, further comprising the step of removing the composition from the target area after administration.

12. The method of claim 1, wherein the mammal is a human.

13. The method of claim 12, wherein the alopecia is selected from the group consisting of alopecia areata, hair loss secondary to chemotherapy or radiation treatment, stress-related hair loss, self-induced hair loss, and scarring alopecia.

* * * * *